(12) United States Patent
Hunzinger

(10) Patent No.: US 7,257,419 B2
(45) Date of Patent: Aug. 14, 2007

(54) METHOD FOR ATTEMPTING TO ESTABLISH A CONNECTION BETWEEN A MOBILE STATION AND A WIRELESS COMMUNICATION SYSTEM INCLUDING A PARAMETER IDENTIFYING REASON FOR A PREVIOUSLY FAILED RECONNECTION ATTEMPT AND A PARAMETER INDICATING A NUMBER OF TIMES THAT THE REASON OCCURRED

(76) Inventor: Jason F. Hunzinger, 3425 Calle del Sur, Carlsbad, CA (US) 92009

( * ) Notice: Subject to any disclaimer, the term of this patent is extended or adjusted under 35 U.S.C. 154(b) by 0 days.

(21) Appl. No.: 11/324,364

(22) Filed: Jan. 3, 2006

(65) Prior Publication Data

US 2006/0116145 A1  Jun. 1, 2006

Related U.S. Application Data

(62) Division of application No. 10/999,288, filed on Nov. 29, 2004, now Pat. No. 7,024,217, which is a division of application No. 10/029,609, filed on Dec. 20, 2001, now Pat. No. 6,845,245.

(60) Provisional application No. 60/258,620, filed on Dec. 22, 2000.

(51) Int. Cl.
*H04B 7/00* (2006.01)

(52) U.S. Cl. ............... 455/510; 455/436; 455/515; 370/229; 370/230

(58) Field of Classification Search .......... 455/450, 455/510, 436, 437, 515, 514, 434, 516, 525, 455/561, 464, 435.1, 67.11, 435.2, 435.3, 455/424, 425, 575.1, 439, 550.1, 422.1, 452.2, 455/404.2, 414.2, 445, 458, 414.3, 423; 340/311.2, 340/313, 331, 332; 379/93.02, 60, 67.1, 379/10–23, 25, 27; 370/321, 332, 201, 209, 370/350, 450, 362, 363, 364, 522, 352, 351, 370/216, 252, 328, 329; 714/748, 749
See application file for complete search history.

(56) References Cited

U.S. PATENT DOCUMENTS

| 4,811,380 | A | * | 3/1989 | Spear ..................... 455/437 |
|---|---|---|---|---|
| 4,977,612 | A |  | 12/1990 | Wilson |
| 5,230,082 | A |  | 7/1993 | Ghisler et al. |
| 5,276,911 | A |  | 1/1994 | Levine et al. |
| 5,487,155 | A | * | 1/1996 | Drewry et al. ............. 370/438 |
| 5,608,643 | A | * | 3/1997 | Wichter et al. ............. 700/244 |
| 5,794,149 | A |  | 8/1998 | Hoo |
| 5,953,673 | A | * | 9/1999 | Neubauer et al. ........... 455/518 |
| 5,995,830 | A | * | 11/1999 | Amin et al. ................ 455/423 |
| 5,999,816 | A |  | 12/1999 | Tiedemann, Jr. et al. |
| 6,011,978 | A |  | 1/2000 | Ault et al. |
| 6,112,089 | A |  | 8/2000 | Satarasinghe |

(Continued)

*Primary Examiner*—Edward F. Urban
*Assistant Examiner*—Charles Chow
(74) *Attorney, Agent, or Firm*—Harness, Dickey & Pierce, PLC

(57) ABSTRACT

A wireless communication system wherein wireless infrastructure adapts access parameters and manages channel resources based on detailed reconnection information obtained from individual mobile stations. Mobile stations transmit particular reconnection attempt status information to the wireless infrastructure. The reconnection attempt status information, along with the aggregate statistics of other mobile stations, is used by the infrastructure to adapt access parameters to increase or decrease the likelihood of successful access. This allows the infrastructure to tune access parameters to particular mobile station information and it also allows the infrastructure to provide better resource management for both traffic channel assignments and access channel usage.

17 Claims, 4 Drawing Sheets

U.S. PATENT DOCUMENTS

| | | | |
|---|---|---|---|
| 6,215,782 B1 * | 4/2001 | Buskens et al. | 370/350 |
| 6,343,216 B1 * | 1/2002 | Kim et al. | 455/450 |
| 6,445,921 B1 * | 9/2002 | Bell | 455/426.1 |
| 6,477,373 B1 * | 11/2002 | Rappaport et al. | 455/436 |
| 6,501,947 B1 | 12/2002 | Hunzinger et al. | |
| 6,594,485 B1 * | 7/2003 | Ezaki | 455/417 |
| 6,721,557 B1 * | 4/2004 | Ritter | 455/423 |
| 6,766,173 B1 * | 7/2004 | Chun et al. | 455/450 |
| 7,024,217 B2 * | 4/2006 | Hunzinger | 455/510 |
| 2002/0082032 A1 | 6/2002 | Hunzinger | |
| 2002/0099788 A1 * | 7/2002 | Szymansky | 709/217 |
| 2002/0111138 A1 * | 8/2002 | Park | 455/41 |
| 2005/0048981 A1 * | 3/2005 | Anupam et al. | 455/445 |

* cited by examiner

METHOD FOR ATTEMPTING TO ESTABLISH A CONNECTION BETWEEN A MOBILE STATION AND A WIRELESS COMMUNICATION SYSTEM INCLUDING A PARAMETER IDENTIFYING REASON FOR A PREVIOUSLY FAILED RECONNECTION ATTEMPT AND A PARAMETER INDICATING A NUMBER OF TIMES THAT THE REASON OCCURRED

CROSS-REFERENCE TO RELATED APPLICATIONS

This application is a divisional of U.S. patent application Ser. No. 10/999,288 filed on Nov. 29, 2004 now U.S. Pat. No. 7,024,217 which is a divisional of U.S. patent application Ser. No. 10/029,609 filed Dec. 20, 2001, now U.S. Pat. No. 6,845,245 issued Jan. 18, 2005 which claims benefit of U.S. Provisional Application No. 60/258,620 filed Dec. 22, 2000. The disclosures of the above applications are incorporated herein by reference.

TECHNICAL FIELD

This invention relates to wireless communication systems, and more particularly to enhanced handoff control for wireless communication systems.

BACKGROUND

Cellular telephones may operate under a variety of standards including the code division multiple access (CDMA) cellular telephone communication system for which a $2^{nd}$ generation system is described in TIA/EIA, IS-95, Mobile Station-Base Station Compatibility Standard for Dual-Mode Wideband Spread Spectrum Cellular System, published July 1993 and a $3^{rd}$ generation system is described in TIA/EIA, IS-2000-A Volumes 1 through 6. CDMA is a technique for spread-spectrum multiple-access digital communications that creates channels through the use of unique code sequences. In CDMA systems, signals can be and are received in the presence of high levels of interference. The practical limit of signal reception depends on the channel conditions, but CDMA reception in the system described in the aforementioned IS-95 Standard can take place in the presence of interference that is 18 dB larger than the signal for a static channel. Typically, the system operates with a lower level of interference and dynamic channel conditions.

A mobile station utilizing one of the CDMA standards utilizes a set of reverse channels to transmit data to the infrastructure and a set of forward channels to receive data from the infrastructure. Reverse channels include but are not limited to an Access Channel and one or more Traffic Channels. The Access Channel is used by mobile stations for communicating usually short messaging signals to a specific base station, where such signals include but are not limited to call originations, responses to infrastructure pages and system registrations. The various Access Channel messages are comprised of a message body, a message length indicator and a cyclic redundancy check (CRC). Access Channel messages are contained in a data structure called an Access Probe. An Access Probe comprises a preamble and an Access Channel message. Access Probes are sent in sequences containing the same message until an acknowledgement to the message is received. A mobile station will usually increase the power of each successive Access Probe until it receives an acknowledgment to the message or the access parameters affecting transmit power are modified by the base station. The entire process of sending one Access Channel message and receiving (or failing to receive) an acknowledgment is known as an Access Attempt.

A typical mobile-originated connection setup scenario involves the use of multiple signaling messages on multiple channels. The mobile station detects input from the user, for example through keypad or voice detection. The mobile station then initiates an Access Attempt by transmitting an origination message encapsulated in a sequence of Access Probes to a base station. The mobile station will continue transmitting Access Probes containing the same origination message until it receives an acknowledgement on the Forward Paging Channel from the base station that the Access Probe was transmitted to. When the base station receives one of the Access Probes, and resources are available, it responds by setting up a Forward Traffic Channel (defined by an orthogonal code such as a Walsh Code, or a Quasi-Orthogonal Function), transmitting null traffic data on the traffic channel and transmitting a channel assignment message (including the acknowledgement) on the Paging Channel. However, if resources are not readily available, the base station will transmit the acknowledgement along with Access Parameter instructions to the mobile station on the Paging Channel. Access parameter instructions can include, but are not limited to, changes in persistence parameters, access probe power parameters, acknowledgement timeout parameters, number of access probes per sequence or other well known access parameters. The mobile station will continue its Access Attempt, as modified by the Access Parameter instructions received from the base station, until a connection is established.

The connection scenario described above can require many messages and, hence, can consume a large amount of network capacity. Therefore, any way of consolidating this process, thereby conserving capacity, would be welcomed by network operators and be appreciated by users due to fast connection setup.

As discussed above, connection setup can be a process involving multiple reconnection attempts by the mobile station utilizing several Access Probe sequences. It can also involve base station adaptation of Access Parameters, especially when network resources are limited. An Access Probe containing an origination message generally contains a preamble and the origination message which contains information regarding what type of connection is being requesting, the capabilities of the requesting mobile station and other overhead parameters. The base station must manage the access channel parameters and traffic channel assignments based on a very limited knowledge of a particular mobile station state. This invention provides a way for a base station to intelligently adapt access parameters and manage channel assignments based on individual mobile station information.

SUMMARY

The invention consists of a method allowing a wireless infrastructure to adapt mobile station Access Parameters and manage limited channel resources based on detailed reconnection information obtained from individual mobile stations.

The invention involves a mobile station transmitting particular reconnection attempt status information, such as the number of attempts so far and the reason(s) for the reconnections to the wireless infrastructure. A base station, or other infrastructure component, uses this information along with the aggregate statistics of other mobile stations to determine if a particular variation in access parameters can (or has in the past) increase or decrease the possibility of successful access. This allows the wireless infrastructure to use these statistical results, or predefined instructions and parameter values, to tune the access parameters based on a particular mobile station's state information. It also allows the wireless infrastructure to provide better resource management for both traffic channel assignments and access channel usage.

DESCRIPTION OF DRAWINGS

These and other features and advantages of the invention will become more apparent upon reading the following detailed description and upon reference to the accompanying drawings.

DETAILED DESCRIPTION

Figure 1:
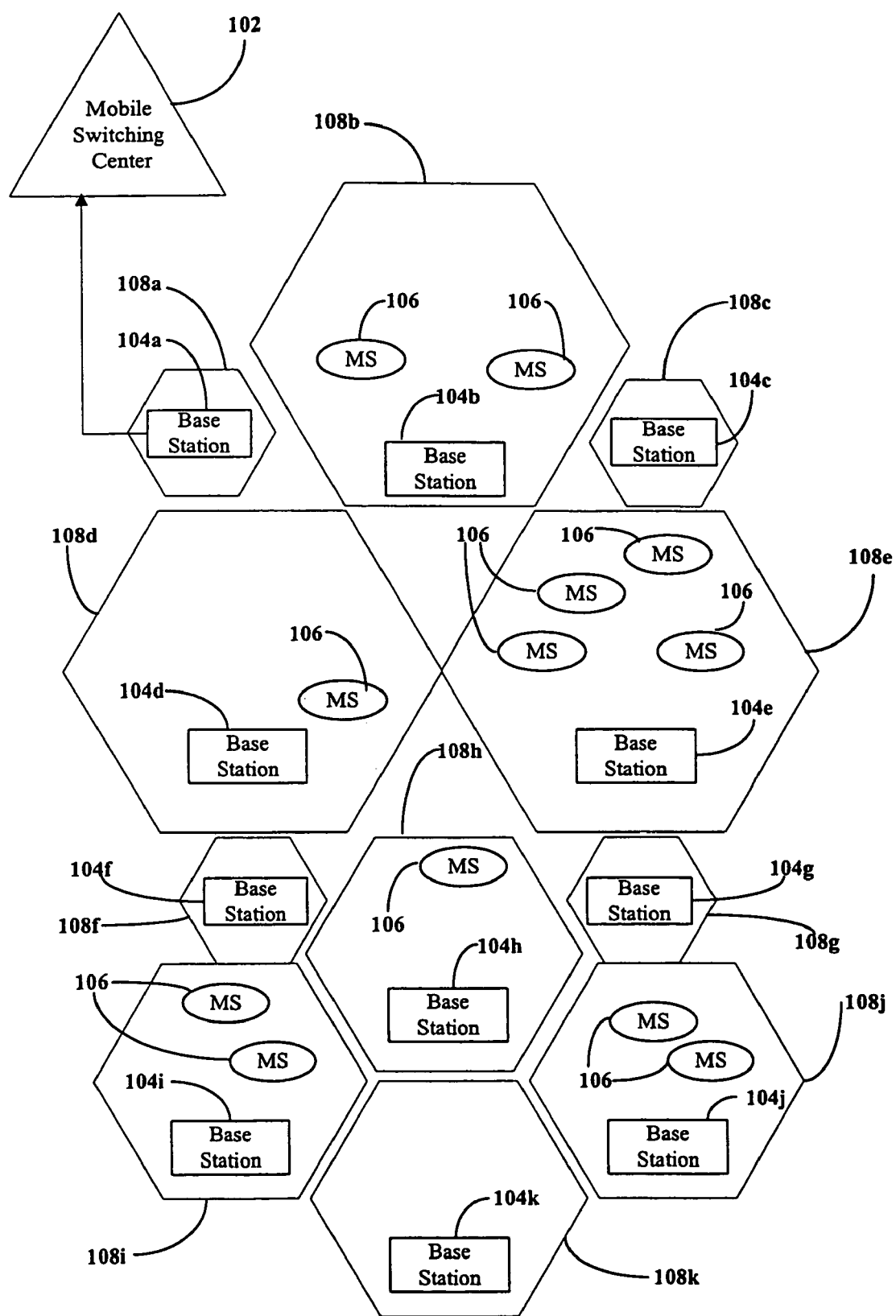
FIG. 1 illustrates the components of an exemplary wireless communication system used by one embodiment of the present invention.

FIG. 1 illustrates components of an exemplary wireless communication system 100. A mobile switching center 102 communicates with base stations 104a-104k (only one connection shown). The base stations 104a-104k (generally 104) broadcasts data to and receives data from mobile stations 106 within cells 108a-108k (generally 108). The cell 108, corresponding to a geographic region, is served by a base station. Practically, said geographic regions often overlap to a limited extent.

A mobile station 106 is capable of receiving data from and transmitting data to a base station 104. In one embodiment, the mobile station 106 receives and transmits data according to the Code Division Multiple Access (CDMA) standard. A set of standards that define a version of CDMA that is particularly suitable for use with the invention include IS-95, IS-95A, and IS-95B, Mobile Station-Base Station Compatibility Standard for Dual-Mode Spread Spectrum Systems; TIA/EIA/IS-2000-2, Physical Layer Standard for cdma2000 Spread Spectrum Systems; and TIA/EIA/IS-2000-5 Upper Layer (Layer 3) Signaling Standard for cdma2000 Spread Spectrum Systems, all of which are herein incorporated by reference in their entirety. CDMA is a communication standard permitting mobile users of wireless communication devices to exchange data over a telephone system wherein radio signals carry data to and from the wireless devices.

Under the CDMA standard, additional cells 108a, 108c, 108d, and 108e adjacent to the cell 108b permit mobile stations 106 to cross cell boundaries without interrupting communications. This is so because base stations 104a, 104c, 104d, and 104e in adjacent cells assume the task of transmitting and receiving data for the mobile stations 106. The mobile switching center 102 coordinates all communication to and from mobile stations 106 in a multi-cell region. Thus, the mobile switching center 102 may communicate with many base stations 104.

Mobile stations 106 may move about freely within the cell 108 while communicating either voice or data. Mobile stations 106 not in active communication with other telephone system users may, nevertheless, scan base station 104 transmissions in the cell 108 to detect any telephone calls or paging messages directed to the mobile station 106. Mobile stations 106 can also initiate a connection by transmitting an origination message to a particular base station sector 104 that it is scanning.

One example of such a mobile station 106 is a cellular telephone used by a pedestrian who, wishing to establish a connection, powers on the cellular telephone while walking in the cell 108. The cellular telephone scans certain frequencies (frequencies known to be used by CDMA) to synchronize communication with the base station 104. The cellular telephone then registers with the mobile switching center 102 to make itself known as an active user within the CDMA network.

When originating a connection the cellular telephone detects input from the user, for example through keypad or voice detection. A connection as referred to herein includes, but is not limited to, voice, multimedia video or audio streaming, packet switched data and circuit switched data connections, short message sequences or data bursts, and paging. The cellular telephone then initiates an Access Attempt by transmitting an origination message encapsulated in a sequence of Access Probes to base station 104. The cellular telephone will continue transmitting Access Probes containing the same origination message until it receives an acknowledgement on the Forward Paging Channel from the base station 104 that the Access Probe was transmitted to. When the base station 104 receives one of the Access Probes, and resources are available, it responds by setting up a Forward Traffic Channel (defined by an orthogonal code such as a Walsh Code, or a Quasi-Orthogonal Function), transmitting null traffic data on the traffic channel and transmitting a channel assignment message (including the acknowledgement) on the Paging Channel. However, if resources are not readily available, the base station 104 will transmit the acknowledgement along with Access Parameter instructions to the cellular telephone on the Paging Channel. Access parameter instructions can include, but are not limited to, changes in persistence parameters, access probe power parameters, acknowledgement timeout parameters, number of access probes per sequence or other well known access parameters. The cellular telephone will continue its Access Attempt, as modified by the Access Parameter instructions received from the base station 104, until a connection is established.

Figure 2:
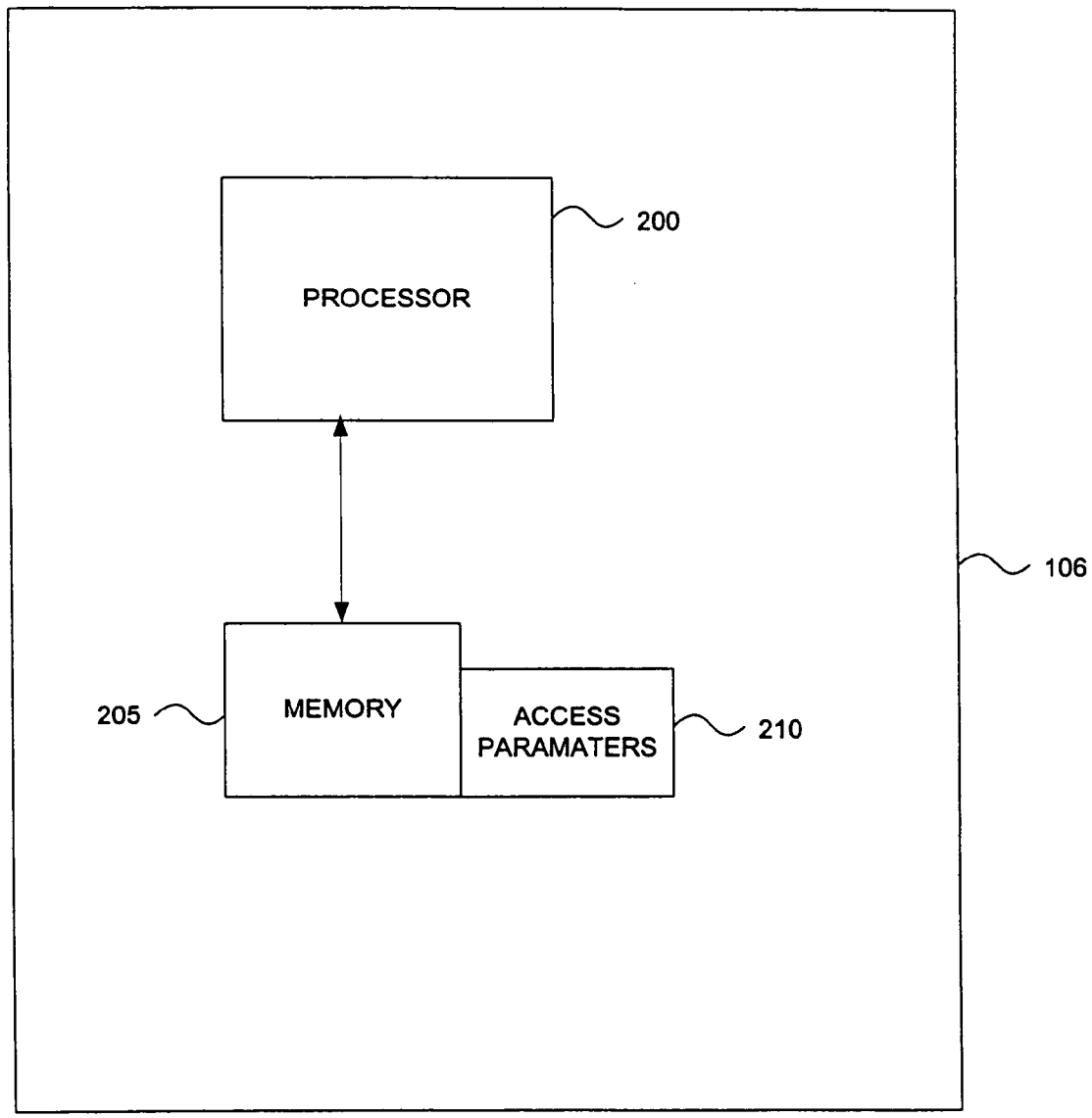
FIG. 2 is a block diagram showing features of a mobile station according to one embodiment of the invention.

FIG. 2 shows a block diagram of the mobile station 106 and the processing that occurs in that mobile station 106. A program stored in a memory 205 drives the processor 200. Access parameters that control the actions taken by the mobile station with regard to use of the access channel may be stored in memory 210.

The present invention involves each mobile station or a subset of all mobile stations served by a base station (or a sector of a base station) transmitting reconnection information to the base station while attempting to establish mobile originated connections. The reconnection information includes, but is not limited to, the reason for the reconnection, the number of reconnection attempts transmitted, the Access Probe power level and the Access Probe Number. The reasons for the reconnection include, but are not limited to, no response from the base station (access failure), and refusal of channel assignment from the base station (access retry). In one embodiment of the present invention, if there is an access failure, then the reconnection information is input to the access parameter tuning algorithm. In another embodiment, if there is an access retry rejection, then the reconnection information goes into the resource management process that prioritizes re-connections/connections. In one embodiment, the number of reconnection attempts include only the number that have occurred (including the current one) for the same reconnect reason as the current one. In another embodiment, the number includes only the consecutive reconnection attempts occurring for the same reason as the current one. The later embodiment could be useful to include in the aggregate statistics since only repetitive problems are accented with high numbers.

Figure 3:
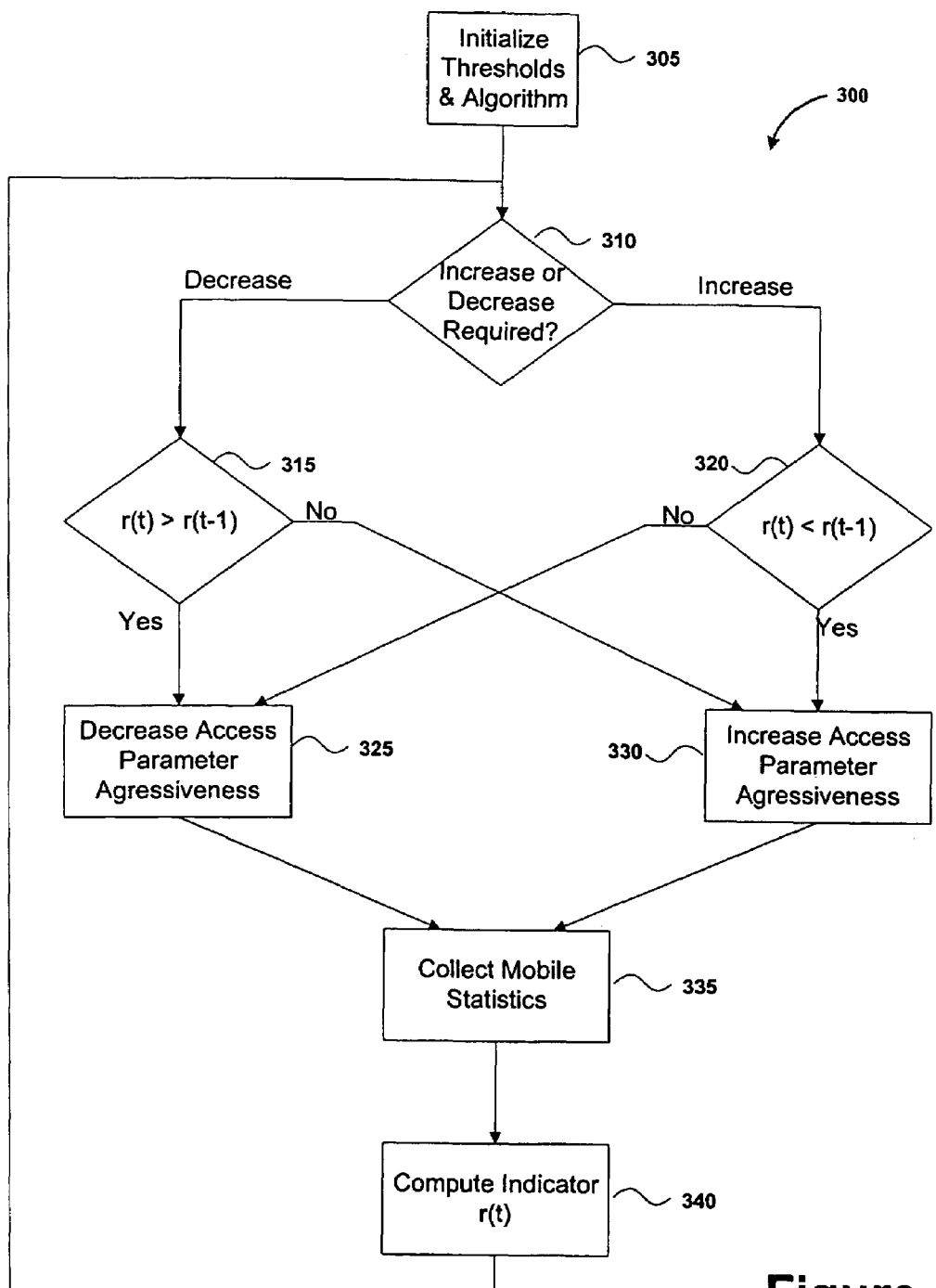
FIG. 3 illustrates a process for tuning access parameters according to one embodiment of the present invention.

The reconnection information described above can be collected by the infrastructure and used to adapt the access parameters to allow for faster connection setup. This adaptation can be performed on the base access parameters that are transmitted to all mobile stations served in the area of interest or can be access parameters that affect only one mobile station, or a subset of mobile stations can be individually tuned. FIG. 3 illustrates a process 300 for tuning access parameters according to one embodiment of the present invention. The process first initializes the threshold and algorithm parameters 305. In one embodiment the thresholds are upper and lower hysteresis levels of access success. In another embodiment the hysteresis levels are lower and upper bounds on distribution of number of retries. The algorithm parameters will depend on the specific indicator algorithm used and an example embodiment will be described below. The process 300 will be described without regard to the specific indicator algorithm. FIG. 3 shows an embodiment where the algorithm exhibits an inverse correlation to success rate (i.e. as success rate increases, the indicator algorithm decreases and vice-versa).

After the initialization 305, the process checks the current indicator against the upper and lower hysteresis levels to determine if an increase or decrease in access parameter aggressiveness is needed 310. If the indicator is less than the lower hysteresis level, then a decrease is necessary and the process proceeds to 315. If the indicator is greater than the upper hysteresis level, then an increase is necessary and the process proceeds to 320. If neither hysteresis level is violated (i.e. the indicator is between the lower and upper hysteresis levels), the process may optionally proceed to 335 (path not shown in FIG. 3) to collect statistics on current mobile station information. In 315 and 320, the process compares the most recent indicator value to the previous indicator value (or a filtered value of past indicator values). If this is the first time attempting to decrease 315 or increase 320 aggressiveness, the comparisons 315 and 320 are skipped and the access parameter aggressiveness is decreased 325 or increased 330 respectively. If the comparison 315 shows that the current indicator is greater than the past indicator value (but a decrease is still needed since the process already proceeded to 315) then the access parameter aggressiveness is decreased further. If the comparison 315 shows that the current indicator is less than the past indicator value (indicating that the decreased aggressiveness parameters did not have the desired effect) then the process proceeds to 330 where the parameter aggressiveness is increased (possibly by simply resetting them to the values prior to the last decrease). A similar procedure occurs in the increased aggressiveness path of 320 and 330. After the Access Parameters are decreased 325 or increased 330, the process proceeds to 335 where the most recent mobile stations reconnection information statistics are collected. After collecting statistics, the access success indicator values are computed for mobile stations 340. The process then proceeds to 310 where the just computed access success indicators are compared to the threshold levels and the process repeats. An example of an indicator that has an inverse correlation with access success is the percentage of retries that take more attempts than is considered ideal.

The access success indicator discussed above can take many forms. In general the indicator must be chosen so that it has a strong correlation with the access success rate. An example embodiment of an indicator with a strong correlation to access success rate follows.

In one embodiment, the mobile station may keep track of how many retries have occurred for each re-connection attempt. This information may be stored locally in a database and an average may be computed. The mobile station may categorize the data according to number of retries. Consider denoting the set of all reconnections received by a base station and labeled as access failures because there was no response received at the mobile as the set R, and denoting the set of attempts that were the j'th retry attempt of a connection as the set $R_j$. The ratio of reconnections that required j reconnection attempts can be computed as the size of the set $R_j$ minus the size of the set $R_{(j+1)}$ (i.e. the number of j'th retries less the number of (j+1)'th retries) over the total number of reconnections. Denoting set size, or cardinality, by vertical bars, the ratio r can be written as $r_j=(|R_j|-|R_{j+1}|)/R_0$. In one embodiment, the system may examine the distribution of $r_j$ across the parameter j. The system may be tuned, or tune itself such that $r_j$ falls off after a threshold value k. For example, if k=3, then no more than 3 retries are generally required to reconnect and $r_{k+1}$ is much less than $r_k$. The system may tune itself using an algorithm that examines the parameter $r_k$ and $r_{k+1}$ and adjusting access or reconnect parameters to tune the distribution of r. Alternatively, in another embodiment, the system may tune itself by examining the parameter $r_1$ (i.e. r at a specific point 1) as time varies and as the system adapts. For example, the system may attempt an adaptation step of increasing or decreasing the aggressiveness of access parameters and then examine if the statistic $r_1$ has adjusted in the desired direction. Note that 1 may be set equal to k, k+1 or any other threshold or number of retries of interest. The indicator in FIG. 3 may be considered, for example, as $r_k(t)$, where t is the current time. Alternatively, the indicator in FIG. 3 may be considered, for example, as r(t) where t=k or t=k+1. In this latter example, the decision blocks 315 and 320 are determining if the desired relationship between number of retries, i.e. fall-off after k retries, exists or if adaptation is required.

Access parameter aggressiveness may be increased by increasing the initial power level, power step size, number of access probes, number of probe sequences, or any other access related parameter that may increase the chance of a base station receiving the mobile station access transmission sooner. Increasing access parameter aggressiveness may involve considering the tradeoff of interference implications due to higher power transmissions. Ideally, the number of access transmissions or duration of access transmissions should be minimized while also minimizing the time until the power level reaches and does not overly exceed a level receivable by the base station. The purpose of increasing access parameter aggressiveness is to improve the chances that a mobile station transmission is received as soon as possible by a base station without excess interference in the reverse link.

Decreasing access parameter aggressiveness may include lowering initial power level, power step size, number of access probes, number of probe sequences, or any other access related parameter that may decrease the chance of mobile transmissions that are unnecessarily long or strong while maintaining a satisfactory chance of a base station receiving the mobile station access transmission within a satisfactory time period. The purpose of decreasing access parameter aggressiveness is to reduce the chance of unnecessary interference through unnecessarily strong, long, or number of access transmissions.

The access probing method is designed to start at a relatively low power and increase power of transmissions until the base station receives the mobile station transmission. The access parameters may be initially configured by a network engineer to correspond to average signal environment conditions within a sector or cell. A single set of access parameter values may not be ideal for all conditions. The ideal parameter values may vary with time, location, mobile station, and other environmental or user characteristics. Adaptation of access parameters may take into account variation in the ideal values by using a hysteresis method. In such a method threshold levels may be established about the desired access performance so that the parameters are only tuned if the performance is worse or better than the respective hysteresis bounds.

The infrastructure may also use the access retry information transmitted by the mobile for resource management/planning (as opposed to the access failure information that was used in the access parameter tuning process above). The access retry information corresponds to those reconnection attempts that are made due to refusal by the infrastructure to allocate a traffic channel. This may be particularly useful for packet data connections. The base station may respond differently to each mobile depending on how many access retry attempts the mobile has made so far. For example, the base station could ask the mobile to wait longer before trying to reconnect next time. The base may use statistics about how many pending connections there are and how long they have been pending to release and re-assign resources.

In one embodiment, the infrastructure may keep track of pending connections that were requested to reattempt in the future. The infrastructure may thereby optimally re-schedule future new connection requests. The infrastructure may also maintain a database of connection durations correlated with the type of connection, user or other characteristic and use this information to predict the end of connections. This information can further be used as input for determining how long to ask a terminal requesting a new connection or reconnection to wait until retrying.

Figure 4:
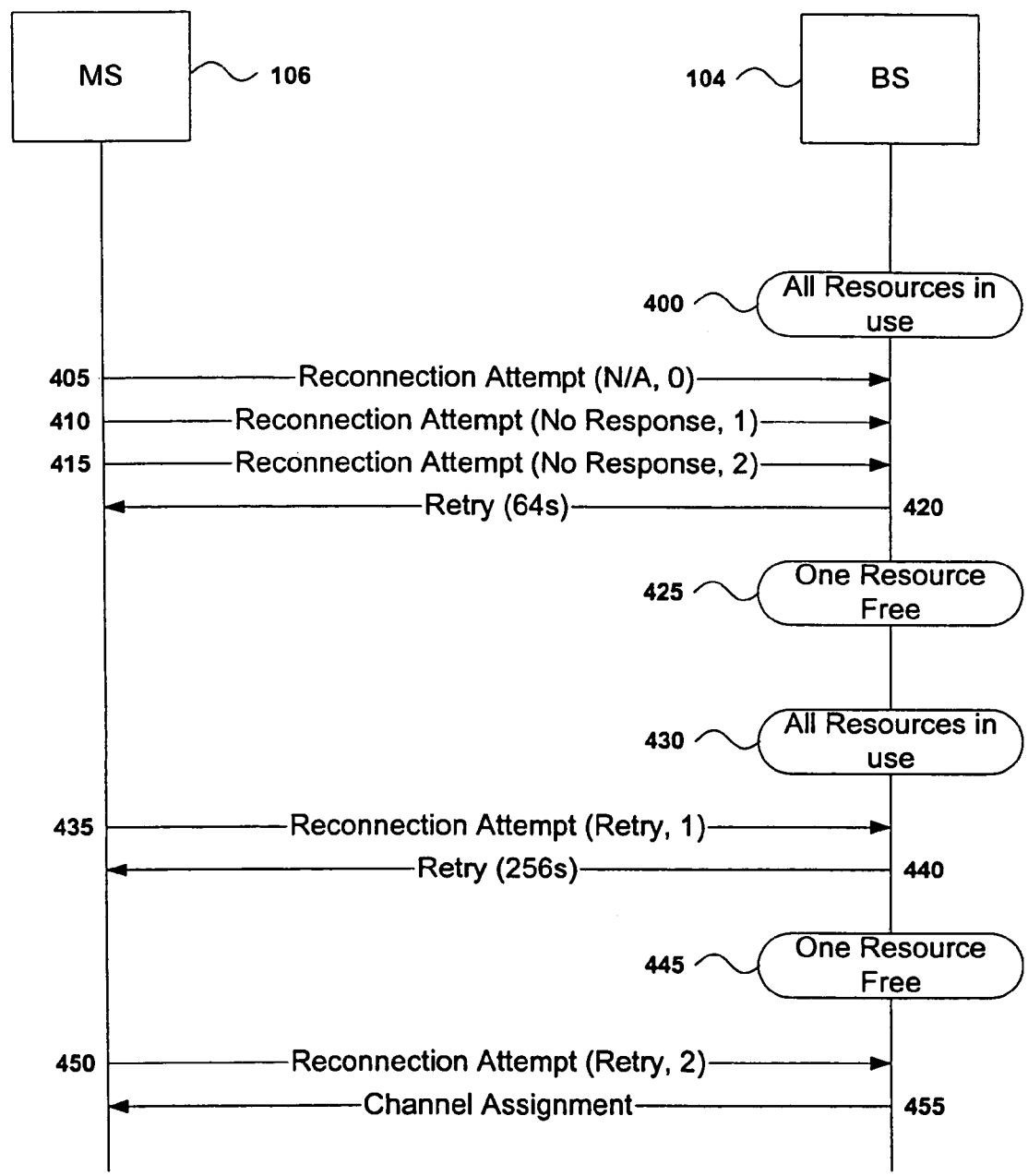
FIG. 4 illustrates an example of a connection/reconnection process according to one embodiment of the present invention.

FIG. 4 shows an example of using both the mobile station reasons for reconnection (either access failures or access retries) and the number of failed retry attempts of that type to control when the mobile retries. A mobile station 106 is attempting to set up a connection to a base station 104. The base station's resources (e.g. traffic channels) at the start of the access attempt are all in use 400. The mobile station transmits an access probe containing an origination message, which includes, among other data, a reconnection attempt 405. The reconnection attempt contains the reason for the reconnection and the number of times that this type of failure has occurred. Since 405 is the first attempt to set up a connection, the reason is N/A and the number of times is zero. After waiting for an acknowledgement from base station 104 for the required amount of time, the mobile station 106 transmits a second reconnection attempt 410 containing a "No Response" reason indicating an access failure and a number one indicating that this is the first reconnection due to an access failure. After waiting for an acknowledgement from the base station 104, the mobile station transmits a third reconnection attempt 415 containing a "No Response" reason and a number 2 indicating that this is the second reconnection attempt of the "No Response" type. Since no resources are available, the base station, after successfully receiving attempt 415, transmits an origination response message 420 containing an indicator to the mobile station 105 that it should retry the reconnection in 64 seconds. The base station can use the reconnection information contained in 415 to adapt access parameters in the future as presented for the access parameter tuning algorithm. One resource temporarily becomes available 425 before the mobile station's 64 second delay period elapses. The resources are once again all in use at 430. After waiting the instructed 64 seconds, the mobile station transmits a reconnection attempt 435 containing the reason "Retry" and the number 1 indicating that this is the first reconnection attempt because of an access retry. Since all resources are in use, the base station, after successfully receiving message 435, transmits an origination response message 440 containing instructions for the mobile station to wait 256 seconds before attempting a reconnection. The base station can use the reconnection information contained in 435 for future resource management and planning. Before the 256 second timer expires, a resource becomes available 445. The mobile station transmits a reconnection attempt containing the reason "Retry" and the number 2 indicating that this is the second reconnection attempt resulting from an access retry. After successfully receiving message 450, the base station 104 transmits an origination response message containing a channel assignment that sets up a traffic channel for mobile station 106. The base station 104 can also use the reconnection information in 450 for use in future resource management and planning strategies. Thus, the mobile station 106 concludes a successful access attempt.

Note also that embodiments of the present invention can be generalized to communications protocols other than CDMA. Systems incorporating TDMA or FDMA or combinations of both can easily adapt the connection access methods to include the present invention. Note also, that systems other than cellular telephone systems, such as adhoc wireless networks, wireless LAN and WAN networks could also utilize the present invention.

Numerous variations and modifications of the invention will become readily apparent to those skilled in the art. Accordingly, the invention may be embodied in other specific forms without departing from its spirit or essential characteristics.

What is claimed is:

1. A method for attempting to establish a connection between a mobile station and a wireless communication system comprising:

transmitting a plurality of reconnection attempt messages, each containing a parameter identifying a reason for a previously failed reconnection attempt and a parameter indicating a number of times that the reason has occurred;

attempting to receive the plurality of reconnection attempt messages and, if the attempt to receive succeeds, storing the parameter identifying the reason for the previously failed reconnection attempt and the parameter indicating the number of times that the reason has occurred.

2. The method of claim 1, wherein the reason for the previously failed reconnection attempt is one of the group consisting of an access failure, a lack of resources, an acknowledgment failure, a connection denial, and lack of channel assignment.

3. The method of claim 1, further comprising adapting system access parameters using said stored parameters.

4. The method of claim 3, further comprising computing an indicator correlated to success rate.

5. The method of claim 3, wherein the adapted access parameters are common to a subset of a plurality of mobile stations in a system.

6. The method of claim 3, further comprising computing an indicator inversely correlated to success rate.

7. The method of claim 6, wherein the indicator is a measure of distribution of number of reconnection attempts required to successfully connect.

8. The method of claim 1, further comprising controlling resources using said stored parameters.

9. The method of claim 8, wherein the resources are selected from the group consisting of packet data resources, circuit switched resources, common channels, dedicated channels, forward channels, reverse channels, shared channels, and voice channels.

10. The method of claim 1, further comprising determining a time to re-attempt connection using said stored parameters.

11. The method of claim 1, wherein the parameter indicating a number of times that the reason has occurred identifies a number of consecutive reconnection attempts for the same reason.

12. The method of claim 1, wherein the parameter indicating a number of times that the reason has occurred identifies a number of reconnection attempts for the same service option selection.

13. The method of claim 12, wherein the number of reconnection attempts for the same service option selection is for a current connection only.

14. The method of claim 12, wherein the number of reconnection attempts for the same service option selection is the number of consecutive reconnection attempts for the same service option selection.

15. The method of claim 1, wherein the parameter indicating a number of times that the reason has occurred identifies a number of silent retries.

16. The method of claim 15, wherein the number of silent retries is the number of consecutive silent retries.

17. The method of claim 15, wherein the number of consecutive reconnection silent retries is for the current connection only.

\* \* \* \* \*